(12) United States Patent
Vanpoulle et al.

(10) Patent No.: US 9,220,260 B2
(45) Date of Patent: *Dec. 29, 2015

(54) BIOCIDAL GRANULE, IN PARTICULAR FOR MAKING ASPHALT SHINGLE

(75) Inventors: Sophie Vanpoulle, Gentilly (FR); Christelle Pousse, Paris (FR); Lethicia Gueneau, Cheval Blanc (FR); Philippe Barboux, L'hay les Roses (FR)

(73) Assignee: CERTAINTEED CORPORATION, Valley Forge, PA (US)

( * ) Notice: Subject to any disclaimer, the term of this patent is extended or adjusted under 35 U.S.C. 154(b) by 1660 days.

This patent is subject to a terminal disclaimer.

(21) Appl. No.: 11/910,979

(22) PCT Filed: Apr. 4, 2006

(86) PCT No.: PCT/FR2006/050296
§ 371 (c)(1),
(2), (4) Date: Aug. 6, 2010

(87) PCT Pub. No.: WO2006/106263
PCT Pub. Date: Oct. 12, 2006

(65) Prior Publication Data
US 2010/0303875 A1 Dec. 2, 2010

(30) Foreign Application Priority Data
Apr. 7, 2005 (FR) .................... 05 50899

(51) Int. Cl.
| | | |
|---|---|---|
| *A01N 25/26* | (2006.01) | |
| *B05D 7/00* | (2006.01) | |
| *E04D 1/22* | (2006.01) | |
| *A01P 3/00* | (2006.01) | |
| *A01N 25/12* | (2006.01) | |
| *A01N 25/34* | (2006.01) | |
| *C09C 1/00* | (2006.01) | |
| *C09C 3/00* | (2006.01) | |
| *C09C 3/06* | (2006.01) | |
| *C09C 3/08* | (2006.01) | |
| *C09C 3/12* | (2006.01) | |
| *E04D 13/00* | (2006.01) | |
| *E04D 1/00* | (2006.01) | |

(52) U.S. Cl.
CPC ............... *A01N 25/12* (2013.01); *A01N 25/34* (2013.01); *C09C 1/0081* (2013.01); *C09C 3/006* (2013.01); *C09C 3/063* (2013.01); *C09C 3/08* (2013.01); *C09C 3/12* (2013.01); *E04D 13/002* (2013.01); *C01P 2006/12* (2013.01); *C01P 2006/14* (2013.01); *E04D 2001/005* (2013.01); *Y10T 428/2438* (2015.01); *Y10T 428/24372* (2015.01); *Y10T 428/24388* (2015.01)

(58) Field of Classification Search
None
See application file for complete search history.

(56) References Cited

U.S. PATENT DOCUMENTS

| | | | | |
|---|---|---|---|---|
| 5,356,664 | A * | 10/1994 | Narayan et al. | ............... 427/186 |
| 2004/0064968 | A1 * | 4/2004 | Fain et al. | ....................... 34/467 |
| 2004/0110639 | A1 | 6/2004 | Joedicke | |
| 2007/0148342 | A1 * | 6/2007 | Kalkanoglu et al. | .......... 427/212 |

FOREIGN PATENT DOCUMENTS

| | | | |
|---|---|---|---|
| CA | 1122897 | A1 * | 5/1982 |
| EP | 0 003 302 | A1 | 8/1979 |
| GB | 1214816 | | 12/1970 |
| GB | 1590573 | * | 6/1981 |
| JP | 61-176501 | | 8/1986 |
| JP | 4-352701 | | 12/1992 |
| WO | WO 94/23580 | | 10/1994 |
| WO | WO 00/11949 | | 3/2000 |

* cited by examiner

*Primary Examiner* — David J Blanchard
*Assistant Examiner* — Daniel F Coughlin
(74) *Attorney, Agent, or Firm* — Oblon, McClelland, Maier & Neustadt, L.L.P.

(57) ABSTRACT

The invention relates to biocidal granules composed of a mineral core coated with at least one porous inorganic layer including at least one organic compound capable of limiting or preventing the growth of microorganisms, in particular of algae.

The invention also relates to a sol-gel process for the preparation of the biocidal granules and to the use of these biocidal granules in building materials, in particular shingles and siding coatings.

21 Claims, No Drawings

BIOCIDAL GRANULE, IN PARTICULAR FOR MAKING ASPHALT SHINGLE

The present invention relates to granules exhibiting a biocidal activity, in particular with regard to algae, intended in particular for the preparation of asphalt shingles.

Asphalt shingles are traditionally used in the United States and Canada as exterior covering for the siding or roofing of residential buildings.

Two types of shingles are distinguished, depending on the nature of the reinforcement of which they are composed: "organic" shingles, based on a thick felt of wood fibers or cellulose fibers, and "glass fiber" shingles, the fibers being nonwoven and held together by a water-insoluble binder.

The manufacture of covering organic shingles consists in continuously unwinding the dry felt of organic fibers and in passing it into a storage system composed of several rotating rollers in order to convey it into a first bath of liquid asphalt (temperature of the order of 250° C.). At the other end of the bath, the felt passes into a second storage system in order to allow the felt to absorb excess asphalt and to slightly cool. The impregnated felt is subsequently coated with molten asphalt on both its faces, colored granules are distributed over the upper face and a release agent, for example talc, is applied to the lower face. The combined product passes between the rollers of the cooled calender, so as to partially embed the granules in the hot asphalt, and the product, once cooled, is collected in the form of a winding or of sheets cut to the desired size.

With the exception of the first impregnating stage, which is omitted, the manufacture of glass fiber shingles is carried out under the same conditions.

In the shingle, the main role of the asphalt is to render the material impermeable to water. It also acts as support for the granules and strengthens the material, and its highly ductile nature makes it possible to obtain a flexible product which is easy to use. As a general rule, the lifetime of the shingle increases with the amount of asphalt.

The granules, generally mineral granules, have the role of conferring good durability on the shingle: they protect the asphalt from the effects of solar radiation (in particular ultraviolet rays) and of the environment (attacks from the weather, pollution and the like), and contribute to better light reflection. In addition, the granules are colored, naturally or artificially by the application of pigments, in order to satisfy the aesthetic requirements of the user.

It is commonplace to see the appearance of green-, brown- or black-colored stains at the surface of asphalt shingles on buildings found in regions with a temperate climate. These stains are due to microorganisms, predominantly algae of the genus *Gloeocapsa*, which benefit from conditions favorable to their growth: heat, humidity and a large amount of nutrients, the essential inorganic elements which are contributed by the mineral granules but also the organic matter which is deposited on the shingles. The rather unattractive nature of these stains, which becomes more pronounced as the color of the shingle becomes lighter, is not the only disadvantage: the darkening of the surface, which absorbs solar radiation more, reduces the insulating nature of the material and shortens its lifetime.

One means of overcoming this disadvantage consists in treating the contaminated parts with suitable biocides.

The complete removal of the algae is difficult and requires treating the whole of the building, including apparently healthy surfaces. Even using a powerful biocide, such as sodium hypochlorite, the effect is not permanent due to leaching by rainwater and run-off water. In addition, some green algae, which are particularly resistant to biocides, can recolonize already treated surfaces, for this reason requiring additional treatments at regular intervals in order to restrict their reappearance.

Other known means for preventing the appearance of undesirable stains are based on the incorporation of algicide in the shingle. A proposal has been made to include, in the asphalt, granules incorporating metal compounds in the form of zinc oxide or sulfide (U.S. Pat. No. 3,507,676), of copper oxide (U.S. Pat. No. 5,356,664) or of a mixture of zinc oxide and copper oxide (US-A-2002/0258835 and US-A-2002/0255548).

The proposal has also been made to disperse, at the surface of the shingle, a granular or pulverulent material comprising an algicide (JP-A-2004162482).

In U.S. Pat. No. 6,245,381, the proposal is made to add a biocide, in the salt or chelate form starting from $Cu^{2+}$, $Zn^{2+}$ and $Sn^{2+}$ ions complexed with an anionic organic binder, to the asphalt during the manufacture of the shingle.

There exists a need to have available novel means for preventing the appearance of undesirable colorings on shingles, in particular asphalt shingles.

The present invention provides a biocidal granule composed of a mineral core coated with at least one porous inorganic layer including at least one compound capable of limiting, indeed even preventing, the growth of microorganisms, in particular of algae.

In the granule according to the invention, the mineral core acts as support for the porous layer which, as it were, forms a reservoir for the biocide, which can thus diffuse toward the outside. By virtue of the controlled release effect of the biocide, it is possible to control the growth of the microorganisms on a lasting basis.

The porous layer is composed of an inorganic material chosen from semimetal or metal oxides, such as silica, alumina, zirconia and titanium oxide, or their mixtures. Preferably, silica is chosen.

The porous layer generally exhibits a mean pore diameter of between 1 and 100 nm, preferably between 2 and 50 nm and better still of the order of 5 nm.

The porous layer also exhibits a total pore volume at least equal to $0.5 \times 10^{-3}$ cm$^3$/g for pores with a diameter of less than 100 nm, preferably of less than 0.1 cm$^3$/g, advantageously of between $0.7 \times 10^{-3}$ and $1 \times 10^{-2}$ cm$^3$/g and better still of the order of $1.25 \times 10^{-3}$ cm$^3$/g for pores with a diameter of less than 76 nm.

The specific surface of the porous layer is generally greater than 1 m$^2$/g and preferably varies from 1.25 to 100 m$^2$/g.

The porous layer has a mean thickness at most equal to 20 μm, preferably of between 0.5 and 10 μm, advantageously between 1 and 5 μm. It can be composed of one or more layers, preferably of 1 to 3 layers, each having a thickness of the order of 2 μm.

The biocide present in the porous inorganic layer can be any organic compound known for its ability to limit or prevent the growth of microorganisms. Mention may be made, by way of examples, of aldehydes, formaldehyde condensates, triazines, phenols, carbonic acid esters, amides, carbamates, thiocarbamates, thiocyanates, dibenzamidines, pyridine derivatives, triazoles, thiazoles, isothiazolones, such as isothiazolin-3-ones, N-haloalkylthio compounds, and mixtures of these compounds. Preference is given to isothiazolin-3-ones, in particular 2-(n-octyl)-4-isothiazolin-3-one (OIT) and 4,5-dichloro-2-(n-octyl)-4-isothiazolin-3-one (DCOIT).

The content of biocide in the granule depends on the nature and characteristics of the porous inorganic layer(s), in particular on the available thickness and available pore volume.

Generally, the amount of biocide represents up to 4% by weight of the granule, preferably up to 2.5% and better still up to 1%.

The mineral core can be composed of any chemically inert material capable of acting as support for the porous inorganic layer and additionally exhibiting mechanical properties which allow it to withstand the various operations carried out during the manufacture of the asphalt shingles. Mention may be made, by way of examples, of mineral materials available in the natural state, such as talc, granite, siliceous sand, andesite, porphyry, marble, syenite, rhyolite, diabase, quartz, slate, basalt and seashells, and materials originating from recycled manufactured products, such as bricks, concrete, porcelain and stoneware.

The mineral core is provided in the form of granules, generally obtained by crushing the above-mentioned material(s) and sieving the products obtained, exhibiting a particle size, taken with regard to its greatest dimension, of between 0.2 and 3 mm, preferably 0.4 and 2.4 mm and better still of the order of 1 mm. The mineral core generally has a shape approaching that of a sphere but it can also have the shape of a platelet, that is to say of a relatively flat item with a thickness which is low with respect to its surface area.

Preferably, the mineral core has a low porosity, defined in particular by a pore volume of less than $1 \times 10^{-3}$ cm$^3$/g, measured for a pore diameter of less than 70 nm.

The mean weight of the particles forming the mineral core is generally of between 0.05 and 15 mg, preferably 0.3 to 7 mg.

Before being coated with the porous inorganic layer, the mineral core can be subjected to one or more operations targeted at conferring the desired coloring on it, in particular by the application of one or more colored coating layers comprising a binder, such as an alkali metal silicate, and one or more compounds of the desired color, for example chosen from metal oxide pigments or carbon black. The techniques allowing the application of such colored layers are well known to a person skilled in the art.

The biocidal granule can additionally comprise at least one coating layer covering all or part of the porous layer having the function of delaying the passage of the biocide toward the external environment. The coating layer is permeable to the biocide and preferably exhibits a lower open porosity than that of the underlying porous layer in which the biocide is found. The porosity of the coating layer is lower by at least 20% and by at most 50% than that of the porous layer comprising the biocide.

The coating layer can be composed of an inorganic material, for example of the same nature as that which constitutes the porous layer, or of an organic material, preferably chosen from polymers, such as polyacrylics and polyurethanes.

The biocidal granule according to the invention is obtained by a sol-gel process comprising the stages consisting in treating the mineral core with an inorganic precursor sol capable of forming the porous layer and a biocide and in drying in order to remove the liquid phase.

The formation of porous inorganic material by the sol-gel method is well known. Usually, the term "sol" is understood to mean a dispersion of colloidal particles in a liquid and the term "gel" is understood to mean a rigid network of polymer chains with a length of greater than 1 µm comprising pores with a size of less than 1 µm. Conventionally, the sol-gel method consists in forming an inorganic precursor sol, as is explained later, applying the sol to the surface to be coated, gelling the mixture, so as to form a three-dimensional network of colloidal particles bonded to one another, and removing the liquid phase, in order to obtain the densification or the chemical stabilization of the network of pores.

According to a first embodiment, the biocidal granule is obtained by treating the mineral core with a sol comprising the inorganic precursor as a mixture with the biocide and by then drying at a temperature of between 20 and 80° C., preferably 40 to 70° C. and better still between 50 and 65° C. This embodiment makes it possible to obtain, in a single stage, a granule comprising a "micropore" layer, that is to say exhibiting in particular a pore diameter of between 0.5 and 2 nm, preferably of the order of 1 nm.

According to a second embodiment, which is preferred, the biocidal granule is obtained in several stages consisting in treating the mineral core with an inorganic precursor sol additionally comprising a structuring agent (or template) and introducing an additional stage of calcination of the sol at a temperature sufficient to remove the liquid and the structuring agent before the application of the biocide.

The term "structuring agent (or template)" is understood here to mean a compound which makes it possible to create pores in the network of inorganic material, this compound being decomposed during the calcination stage, generally carried out at a temperature of greater than 200° C., preferably of less than 1000° C., advantageously of between 400° C. and 700° C. and better still of the order of 450° C. The choice of a structuring agent is to be made according to the size of the biocide to be introduced into the pores and must make it possible to obtain, at the end, pores with a larger size than that of the biocide. Mention may be made, as examples of such compounds, of organic polymers, such as poly(oxyalkylene) block copolymers, in particular poly(oxyethylene)-(oxypropylene)-(oxyethylene) triblock polymers, and quaternary ammonium salts, such as cetyltrimethylammonium bromide. The content of these compounds depends on the degree of porosity desired and on the size of the pores. As a general rule, the structuring agent is added in a proportion of 20 to 80% of the weight of the inorganic precursor, preferably 40 to 70%.

This embodiment makes it possible to obtain a "mesopore" layer with a higher porosity than above, in particular including pores having a mean diameter of between 2 and 50 nm, preferably of less than 10 nm.

In a first alternative form, the biocide is applied to the granule coated with the porous inorganic layer in the form of a solution, preferably in a volatile organic solvent which is subsequently removed, for example by evaporation according to any known method.

Mention may be made, as examples of appropriate organic solvent, of alkanes, in particular cyclohexane, alcohols, in particular ethanol, ketones, in particular acetone, and chlorinated compounds, in particular methylene chloride. The biocidal solution can be applied by spraying or by immersing the porous granules in said solution.

In a second alternative form, the biocide is applied to the porous granule from a sol comprising the biocide and an inorganic precursor identical to or different from that from which the porous inorganic layer is obtained. Preferably, the process is carried out by immersing the porous granule in the sol and the liquid is removed by drying under the temperature conditions indicated above for the first embodiment.

The sol employed in either abovementioned embodiment is an aqueous suspension comprising one or more inorganic precursors chosen from alkylsilanes or alkoxysilanes, such as tetramethoxysilane (TMOS), tetraethoxysilane (TEOS) and methyltriethoxysilane (MTEOS), or zirconium, titanium or aluminum chlorides and alkoxides. Conventionally, the sol is treated with an acid, preferably at a temperature of between 20 and 100° C. and in the presence of an alcohol, such as ethanol, for a period of time sufficient to obtain the conversion of the inorganic precursor to the corresponding metal oxide.

The biocidal granule in accordance with the invention can be used to control the growth of microorganisms, in particular of algae, in any type of building material in order to limit the appearance of colored stains harmful from an aesthetic viewpoint. This material can be an organic asphalt shingle, based on wood fibers or on cellulose fibers, a fiberglass asphalt shingle or an organic and/or inorganic siding coating, in particular a mortar.

As already indicated, shingle manufacture is carried out continuously and comprises a stage of impregnation of a felt of natural fibers (wood or cellulose fibers) or a nonwoven mat of synthetic fibers (glass or polymer fibers, such as polypropylene fibers) with hot liquid asphalt, a stage of application of the granules to the face of the felt or mat according to a defined distribution and with partial inclusion in the asphalt before the latter becomes completely solid, and a stage of collecting the final product in the form of a winding on an appropriate support or sheets cut to the desired size.

In the asphalt shingle, the weight of the granules per unit of surface area is generally between 0.5 and 2.5 kg/m², preferably between 1 and 2 kg/m².

The biocidal granule can be used alone or as a mixture with untreated granules, preferably in a proportion of at least 5% by weight of the combined granules and better still of at least 10%.

The asphalt is generally chosen from byproducts derived from the oil industry, such as simple or air-blown pitches or asphalts. It can comprise modifying agents, for example petroleum oils, fractions or residues, polymeric materials, such as block copolymers, for example of styrene-butadiene-styrene type, stabilizing agents or antistatic agents. The total content of these modifying agents generally does not exceed 15% of the total weight of the asphalt composition.

The asphalt can also comprise up to 25% by weight of one or more amorphous polyolefins, for example chosen from atactic polypropylenes or from copolymers of ethylene and propylene. Preferably, the amorphous polyolefins exhibit a softening temperature of between 130 and 160° C.

The asphalt can also comprise a filler, such as calcium carbonate, talc, carbon black or fly ash, preferably in an amount representing 10 to 70% by weight of the asphalt composition.

The examples which follow make it possible to illustrate the invention without, however, limiting it.

EXAMPLES a) Preparation of the Granules

Use is made of granules exhibiting the following characteristics:
rhyolite granules (deposit at Wrentham, Mass., USA) artificially colored white with titanium oxide (2.7% by weight)
mean diameter: 1 mm
mean weight: 1.26 mg
BET specific surface: 0.37 m²/g
total pore volume (diameter<69 nm): $6.07 \times 10^{-4}$ cm³/g A sol is prepared from 22.3 ml of tetraethoxy-silane (TEOS; 99%), 22.1 ml of a 10% v/v ethanolic solution of 2-(n-octyl)-4-isothiazolin-3-one (OIT; 0.2M) and 9 ml of hydrochloric acid at pH=1.25. The sol is hydrolyzed at 60° C. for 1 hour.

50 g of granules are immersed in the sol for 15 minutes. The suspension is filtered and the granules are washed with water and dried at 60° C. for 2 hours.

The granules obtained comprise 0.7% by weight of OIT (measurement carried out by thermogravimetric analysis).

b) Preparation of the Material

A sheet of aluminum (L=10 cm; W=3.75 cm) is used for the deposition thereon of a sheet produced from a mixture of asphalt (32% by weight) and calcium carbonate (68% by weight) of substantially equivalent size and with a thickness of 16 mm. The combination is heated to 149° C. and then the granules are distributed over the asphalt (1.61 kg/m²) and partially embedded in the latter using a roller with a diameter of 14 cm (3 passes). The granules are composed of untreated granules (90% by weight) and of granules obtained under a) (10% by weight).

c) Biocidal Activity

The alga used is *Gloeocapsa* sp. UTEX LB 795 cultured in a 1 liter flask containing 500 ml of Allen's medium, under constant aeration, at 22° C., under fluorescent light (340-380 nm). The culture is stirred (50-70 rpm; 5 to 10 minutes) at regular intervals (3 or 4 days). After culturing for 20 days, the medium comprises of the order of $1 \times 10^6$ spores/ml.

The medium comprising the spores is sprayed over the shingle samples, on the face comprising granules, at a distance of approximately 4 cm. Each sample is placed in a Petri dish (relative humidity of greater than 80%) placed in an oven at 22° C. under the abovementioned illumination conditions. The samples receive daily an amount of Allen's medium sufficient to ensure the survival of the alga.

The living cells are counted by fluorescence detection microscopy (magnification×200). 10 measurements are taken distributed over the entire surface of the sample. From these measurements, the degree of survival is calculated (degree of survival=(number of living cells at time t/number of living cells at t=0)×100). The results appear in table 1, in which the degree of survival of the cells for different incubating times in the presence of granules according to the invention (example 1) and of untreated granules (control) is shown.

Example 2

The procedure is carried out under the conditions of example 1 modified in that the conditions for the preparation of the granules are different.

Preparation of the Granules

A sol comprising 17.8 g of methyltriethoxysilane (MTEOS), 5.4 g of hydrochloric acid (pH 2.5) and 13.8 g of ethanol is prepared. The sol is hydrolyzed at ambient temperature (25° C.) for 2 hours.

10 ml of sol and 20 ml of an ethanolic solution comprising 1.864 g of (ethylene oxide)$_{73}$-(propylene oxide)$_{28}$-(ethylene oxide)$_{73}$ triblock polyether (Pluronic®) PE 6800, sold by BASF) are mixed.

50 g of untreated granules from example 1 are immersed in the abovementioned mixture for 15 minutes. The suspension is filtered and the granules are calcined in an oven under the following conditions:

25° C. to 100° C. over 30 minutes; 100° C. for 2 hours; 100 to 150° C. over 15 minutes; 150° C. for 2 hours; 150 to 175° C. over 15 minutes; 175° C. for 2 hours; 175 to 200° C. over 10 minutes; 200 to 300° C. over 300 minutes; 300° C. for 1 hour; 300 to 450° C. over 150 minutes; 450° C. for 1 hour.

The cooled calcined granules are immersed in the sol of example 1 and treated under the same conditions.

The granules exhibit the following characteristics:
BET specific surface: 1.66 m²/g
total pore volume (diameter<76 nm): $1.25 \times 10^{-3}$ cm³/g
thickness of the porous layer: 2 μm OIT content (measured by thermogravimetric analysis): 0.7% by weight.

The results of the measurements of the biocidal activity appear in table 1.

Example 3

The procedure is carried out under the conditions of example 2 modified in that the OIT content is 0.4% by weight.

The results of the measurements of the biocidal activity appear in table 1.

Example 4

Granules are prepared under the conditions of example 2. The granules obtained after the calcination stage are, after cooling, introduced into a 10% v/v solution of 2-(n-octyl)-4-isothiazolin-3-one (OIT) in cyclohexane for 4 days at ambient temperature (20-25° C.). The mixture is filtered and the granules are washed with cyclohexane and then dried at 60° C. for 2 hours.

The dried granules comprise 2.52% by weight of OIT.

TABLE 1

| | Degree of survival (%) | | | |
|---|---|---|---|---|
| | t = 5 days | t = 8 days | t = 14 days | t = 19 days |
| Ex. 1 | 2.17 | 0 | 0 | 0 |
| Ex. 2 | 0.8 | 0 | 0 | 0 |
| Ex. 3 | 6.46 | 0 | 0 | 0 |
| Control | 51.11 | 34.22 | 27.11 | 31.55 |
| Reference | 4.91 | 0 | 0 | 0 |

The granules of examples 1 to 3 in accordance with the invention exhibit a biocidal activity demonstrated by a lower degree of survival than for the Control not comprising biocide. The degree of survival of the alga is greatly reduced after 5 days and is zero after 8 days of incubation.

This degree is comparable with that which is obtained using a mixture of granules comprising 10% by weight of biocidal granules based on copper oxide (Algae Block™ Copper Roofing Granules sold by 3M).

What is claimed is:

1. A biocidal granule, comprising:
   a mineral core coated with a porous inorganic layer comprising a biocide,
   wherein the porous inorganic layer comprises at least one material selected from the group consisting of silica, alumina, zirconia, and titanium oxide,
   wherein the biocide is an organic compound, which limits or prevents the growth of microorganisms, and
   wherein the porous inorganic layer is obtained by a sol-gel process.

2. The granule of claim 1, wherein the porous inorganic layer has a mean pore diameter of between 1 and 100 nm.

3. The granule of claim 1, wherein the porous inorganic layer has a total pore volume of at least equal to $0.5 \times 10^{-3}$ cm$^3$/g for a pore diameter of less than 100 nm.

4. The granule of claim 1, wherein the inorganic porous layer has a mean thickness at most equal to 20 µm.

5. The granule of claim 1, wherein the biocide is at least one organic compound selected from the group consisting of an aldehyde, a formaldehyde condensate, a triazine, a phenol, a carbonic acid ester, an amide, a carbamate, a thiocarbamate, a thiocyanate, a dibenzamidine, a pyridine derivative, a triazole, a thiazole, an isothiazolone, and an N-haloalkylthio compound.

6. The granule of claim 5, wherein the biocide is an isothiazolin-3-one selected from the group consisting of 2-(n-octyl)-4-isothiazolin-3-one (OIT) and 4,5-dichloro-2-(n-octyl)-4-isothiazolin-3-one (DCOIT).

7. The granule of claim 1, wherein a content of the biocide in the granule is up to 4% by weight, based on a total mass of the granule.

8. A sol-gel process for preparing the biocidal granule of claim 1, the process comprising:
   (A) treating a mineral core with an inorganic precursor sol capable of forming a porous layer and a biocide, to obtain an intermediate granule, and
   (B) drying the intermediate granule, to remove the liquid phase, wherein the sol is an aqueous suspension comprising an inorganic precursor selected from the group consisting of an alkylsilane, an alkoxysilane, a zirconium chloride, a zirconium alkoxide, a titanium chloride, a titanium alkoxide, an aluminum chloride, and an aluminum alkoxide.

9. The process of claim 8, wherein the treating (A) is carried out with the sol comprising the inorganic precursor as a mixture with the biocide, and
   wherein drying is carried out at a temperature of between 20 and 80° C.

10. The process of claim 8, wherein the inorganic precursor sol further comprises a structuring agent and the process further comprises, before treating the core with the biocide in (A), calcinating the sol at a temperature of greater than 200° C.

11. The process of claim 10, wherein the calcinating temperature is between 400 and 700° C.

12. The process of claim 10, wherein the structuring agent is selected from the group consisting of an organic polymer and a quaternary ammonium salt.

13. The process of claim 10, wherein the biocide is applied to the granule coated with the porous inorganic layer in the form of a solution.

14. The process of claim 10, wherein the biocide is applied to the granule coated with the porous inorganic layer from a sol comprising the biocide and an inorganic precursor identical to or different from that from which the porous inorganic layer is obtained.

15. An asphalt shingle comprising the biocide granule of claim 1,
   wherein the asphalt shingle is selected from the group consisting of an organic asphalt shingle comprising wood fibers, an organic asphalt shingle comprising cellulose fibers, and a glass fiber asphalt shingle comprising mineral granules.

16. The shingle of claim 15, wherein a weight of granules per unit of surface area of the shingle is between 0.5 and 2.5 kg/m$^2$.

17. The shingle of claim 15, wherein the biocidal granule is present alone or as a mixture comprising untreated granules.

18. A process for controlling the growth of microorganisms in a building material, the process comprising:
   incorporating the granule of claim 1 into a building material,
   wherein the building material is at least one selected from the group consisting of an asphalt shingle, an organic siding coating, and an inorganic siding coating.

19. The process of claim 18, wherein the siding coating is a mortar.

20. The granule of claim 1, wherein the mineral core has pore volume of less than $1\times10^{-3}$ cm$^3$/g for a pore diameter of less than 70 nm.

21. The granule of claim 1, wherein the mineral core is composed of chemically inert material.

* * * * *

UNITED STATES PATENT AND TRADEMARK OFFICE
CERTIFICATE OF CORRECTION

| | |
|---|---|
| PATENT NO. | : 9,220,260 B2 |
| APPLICATION NO. | : 11/910979 |
| DATED | : December 29, 2015 |
| INVENTOR(S) | : Sophie Vanpoulle et al. |

It is certified that error appears in the above-identified patent and that said Letters Patent is hereby corrected as shown below:

On the title page, Item 54, "BIOCIDAL GRANULE,IN PARTICULAR FOR MAKING ASPHALT SHINGLE" should read --BIOCIDAL GRANULE, IN PARTICULAR FOR THE MANUFACTURE OF ASPHALT SHINGLES--

Signed and Sealed this
Twenty-third Day of August, 2016

Michelle K. Lee
*Director of the United States Patent and Trademark Office*